United States Patent [19]

Wyvratt, Jr.

[11] Patent Number: 4,581,345
[45] Date of Patent: Apr. 8, 1986

[54] AVERMECTIN 8,9-CYCLOPROPYL COMPOUNDS, PHARMACEUTICAL COMPOSITION AND THERAPEUTIC METHODS OF USE

[75] Inventor: Matthew J. Wyvratt, Jr., Mountainside, N.J.

[73] Assignee: Merck & Co., Inc., Rahway, N.J.

[21] Appl. No.: 720,763

[22] Filed: Apr. 8, 1985

[51] Int. Cl.$^4$ .................. A61K 31/71; C07H 17/08
[52] U.S. Cl. ...................................... 514/30; 514/450; 536/7.1; 549/264
[58] Field of Search ............... 536/7.1; 549/278, 264; 514/30, 450

[56] References Cited

U.S. PATENT DOCUMENTS

| | | | |
|---|---|---|---|
| 4,412,991 | 11/1983 | Ormond | 536/7.1 |
| 4,427,663 | 1/1984 | Mrozik | 536/7.1 |
| 4,459,290 | 7/1984 | Kirst et al. | 536/7.1 |

Primary Examiner—Johnnie R. Brown
Attorney, Agent, or Firm—David L. Rose; Michael C. Sudol, Jr.; Mario A. Monaco

[57] ABSTRACT

There are disclosed novel avermectin 8,9-cyclopropyl compounds (also referred to as 8,9-dihydro-8,9-methano avermectin compounds). The 8,9-cyclopropyl compounds are prepared by treating an avermectin compound with an iodohalomethane compound in the presence of an activated form of zinc. The avermectin 8,9-cyclopropyl compounds have utility as anti-parasitic agents and compositions for that use are also disclosed. The compounds are also highly potent insecticides against agricultural pests.

11 Claims, No Drawings

AVERMECTIN 8,9-CYCLOPROPYL COMPOUNDS, PHARMACEUTICAL COMPOSITION AND THERAPEUTIC METHODS OF USE

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13-position with a 4'-($\alpha$-L-oleandrosyl)-$\alpha$-L-oleandrose group. The avermectin compounds and the instant derivatives thereof have a very high degree of anthelmintic and anti-parasitic activity.

Also included in the prior art are certain synthetically modified avermectins such as 22,23-dihydro avermectin B1a/B1b also known as ivermectin.

The avermectin series of compounds, which are isolated from a fermentation broth, have the following structure:

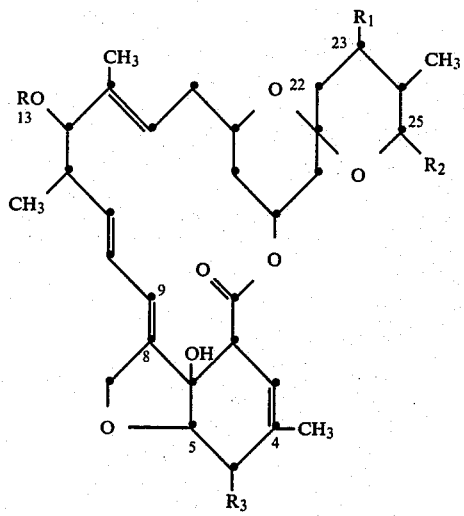

wherein R is the 4'-($\alpha$-L-oleandrosyl)-$\alpha$-L-oleandrose group of the structure:

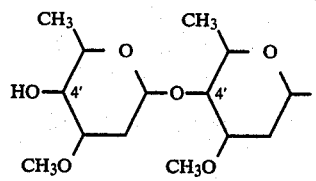

and wherein the broken line indicates a single or a double bond; $R_1$ is hydroxy and is present only when said broken line indicates a single bond;
$R_2$ is iso-propyl or sec-butyl; and
$R_3$ is methoxy or hydroxy.

There are eight different major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'($\alpha$-L-oleandrosyl)-$\alpha$-L-oleandrose):

|     | $R_1$       | $R_2$      | $R_3$   |
| --- | ----------- | ---------- | ------- |
| A1a | Double Bond | sec-butyl  | —OCH$_3$ |
| A1b | Double Bond | iso-propyl | —OCH$_3$ |
| A2a | —OH         | sec-butyl  | —OCH$_3$ |
| A2B | —OH         | iso-propyl | —OCH$_3$ |
| B1a | Double Bond | sec-butyl  | —OH     |
| B1b | Double Bond | iso-propyl | —OH     |
| B2a | —OH         | sec-butyl  | —OH     |
| B2b | —OH         | iso-propyl | —OH     |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

The milbemycin compounds, which have a methyl or ethyl group at the 25-position and lack the 13-disaccharide group are also starting materials for the instant compounds. They are disclosed in U.S. Pat. No. 3,950,360.

SUMMARY OF THE INVENTION

The instant invention is concerned with certain derivatives of avermectin compounds wherein the 8,9 double bond is reacted with an iodohalo-methane to prepare a cyclopropyl group. Thus it is an object of the instant invention to describe such avermectin 8,9-cyclopropyl compounds. A further object is to describe processes for the preparation of such compounds. A still further object is to describe the uses of such compounds as anti-parasitic agents. Still further objects will become apparent from a reading of the following description.

DESCRIPTION OF THE INVENTION

The compounds of the instant invention have the following structural formula.

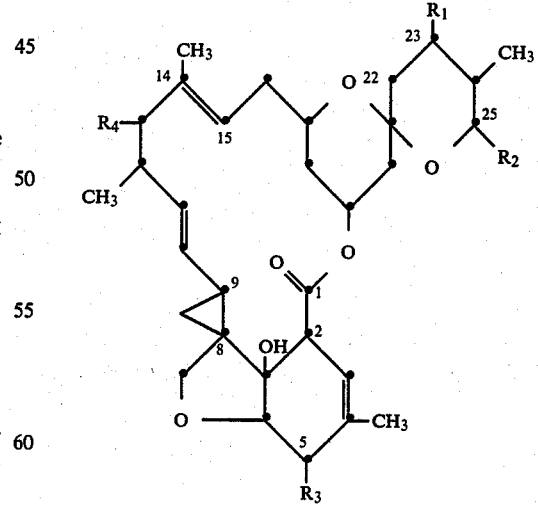

wherein the broken line at the 22,23-position indicates a single or doulbe bond;
$R_1$ is hydrogen of hydroxy provided that $R_1$ is present only when the broken line at the 22,23-position incicates a single bond;

R₂ is methyl, ethyl, iso-propyl or sec-butyl;
R₃ is hydroxy or methoxy;
R₄ is hydrogen, hydroxy,

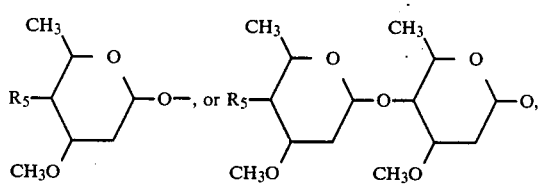

R₅ is hydroxy, keto or —NR₆R₇ and
R₆ and R₇ are independently hydrogen, loweralkyl, loweralkanoyl, loweralkylsulfonyl or substituted benzene sulfonyl, wherein the substituent is halogen.

In the instant description, the term "loweralkyl" is intended to include those alkyl groups containing from 1 to 6 carbon atoms in either a straight or branched chain. Exemplary of such alkyl groups are methyl, ethyl, propyl, isopropyl, butyl, sec-butyl, pentyl, hexyl and the like.

The term "loweralkanoyl" is intended to include those alkanoyl groups of from 2 to 6 carbon atoms of either a straight or branched chain. Such groups are exemplified by acetyl, propionyl, butyryl, pentanoyl, hexanoyl and the like.

The term "halogen" is intended to include the halogen atom, fluorine, chlorine, bromine and iodine.

Examples of preferred compounds of this invention are as follows:

8,9-Dihydro-8,9-methanoavermectin B1a/B1b;
8,9-Dihydro-8,9-methanoavermectin B1a/B1b monosaccharide;
8,9,22,23-tetrahydro-8,9-methanoavermectin B1a/B1b;
8,9,22,23-tetrahydro-8,9-methanoavermectin B1a/B1b monosaccharide;
8,9-Dihydro-8,9-methanoavermectin A1a/A1b;
8,9-Dihydro-8,9-methanoavermectin B2a/B2b;
8,9-Dihydro-8,9-methanoavermectin B1a/B1b aglycone;
13-Deoxy-8,9,22,23-tetrahydro-8,9-methanoavermectin B1a/B1b aglycone;
4"-Amino-4"-deoxy-8,9-dihydro-8,9-methanoavermectin B1a/B1b;
4"-Acetylamino-4"-deoxy-8,9-dihydro-8,9-methanoavermectin B1a/B1b.

The "b" compounds, those with a 25-iso-propyl group, are very difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture is sometimes done by referring to "the B1 or B2 compounds" or by separating the "a" compound from the "b" compound by a slash (/) such as B1a/B1b, B2a/B2b and the like.

The compounds of this invention are prepared by reacting the appropriately substituted starting materials which contain a double bond at an 8,9-position with an iodohalomethane in the presence of an activated form of zinc. The iodohalomethane is preferably diiodomethane. The zinc is prepared in an activated form by preparing an alloy, also referred to as a "couple" with other materials such as copper or silver, preferably copper, as is described in J. Org. Chem., 29 2048 (1964) by E. LeGoff.

The reaction is carried out by adding to the zinc couple suspended in an organic solvent, such as ether or tetrahydrofuran, the avermectin starting material either as a solid or dissolved in the same solvent.

The iodohalomethane is then added and the reaction continued at from room temperature to the reflux temperature of the reaction mixture, refluxing is preferred, for from 2 hours to 2 days or for as long as is required to complete the reaction. The course of the reaction is monitored by such analytical techniques as high pressure liquid chromatography, to determine when the starting material has all been consumed. The zinc couple and the iodohalomethane are both used in excess relative to the avermectin starting materials. From 2 to 15 molar equivalents have generally been found to be satisfactory, although additional quantities of the reagent has not been found to be detrimental. If the reaction appears not to have gone to completion after prolonged refluxing, it is sometimes helpful to add additional quantities of the iodohalomethane reagent and to continue refluxing until the reaction is complete.

The reaction for the preparation of the 8,9-cyclopropyl group may be carried out either before or after the reaction to prepare the substituents at either positions of the avermectin molecule, since there is no conflict between the various types of reactions. Where a hydroxy group is present, however, it is often necessary, particularly at the 5-position, to protect such group. Where the reaction conditions are such as to prepare a cyclopropyl group at one of the other double bonds present on the molecule, the additional product has been found to be readily separable from the desired product. The 8,9-cyclopropyl compounds are isolated using techniques known to those skilled in the art.

PREPARATION OF STARTING MATERIALS

The ultimate starting materials for the compounds of this invention are the avermectin fermentation products defined above which have the isopropyl or sec-butyl group at the 25-position. These compounds with a methyl or ethyl group at the 25-position and no carbohydrate function at the 13-position are often referred to as milbemycin compounds and are disclosed in U.S. Patent 3,950,360 to Aoki et al. Thus it is apparent that additional reactions are required to prepare many of the immediate starting materials for the instant compounds. Specifically, reactions are carried out at the 4", 13, 22, and 23-positions. In addition, during the cyclopropanation reaction described above, it is generally advisable to protect the 5-hydroxy group to prevent the activation and possible cyclopropanation of the 3,4-double bond. In addition, protection of the 5-hydroxy group has been found to facilitate the separation of the various cyclopropyl adducts. With the appropriate positions protected, the cyclopropanation reaction may be carried out without affecting the remainder of the molecule. Subsequent to any of the above described reactions the protecting group may be removed and the unprotected product isolated. The protecting group employed is ideally one which may be readily synthesized, will not be affected by the reaction with the cyclopropanation reagents and may be readily removed without affecting any other functions of the molecule. It is noted that the instant protected compounds are novel and have considerable anti-parasitic activity. They are included within the ambit of the instant invention. One preferred type of protecting group for the avermectin and milbemycin type of molecule is the tri-substituted silyl group, preferably the trialkyl silyl group. One especially preferred example, is the t-butyl dimethylsilyl group. The reaction preparing the protected compound is carried out by reacting the hydroxy, usually the 5-hydroxy, compound with the appropriately substituted silylhalide, preferably the silylchloride in an aprotic polar solvent such as dimethylformamide. Imidazole is added as a catalyst. The reaction is complete in from 1 to 24 hours at from 0 to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions.

The silyl group are then removed after the other reactions have been carried out. The silyl group or groups are removed by stirring the silyl compound in methanol catalized by a catalytic amount of an acid, preferably a sulfonic acid such as p-toluene sulfonic acid. The reaction is complete in about 1 to 12 hours at from 0° to 50° C. Alternatively, the silyl group or groups can be removed with a hydrogen fluoride-pyridine complex in an organic solvent such as tetrahydrofuran. The reaction is complete in from about 3 to 24 hours and is preferably carried out at room temperature.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the "1"-series of compounds. Thus in the "1" series of compounds it is possible to selectively reduce the 22,23 double bond while not affecting the remaining four unsaturations or any other functional group present on the molecule. It is necessary to select a specific catalyst for the hydrogenation, one that will selectively hydrogenate the least hindered from among a series of unsaturations. The preferred catalyst for such a selective hydrogenation procedure is one having the formula:

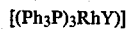

[(Ph₃P)₃RhY)]

wherein
Ph is phenyl and Y is halogen. The reduction procedure is completely described in U.S. Pat. No. 4,199,569 to Chabala et al.

Additional reactions which may be carried out to prepare the compounds of this invention are the selective removal of one of the α-L-oleandrosyl moieties (described in U.S. Pat. No. 4,206,205 to Mrozik et al.).

The reaction conditions which are generally applicable to the preparation of both the monosaccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 0.01 to 10% by volume. The reaction mixture is generally stirred at about 20-40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the monosaccharide and the aglycone. The procedure for the preparation of the monosaccharide uses 1% acid by volume in isopropanol at from 20-40° C., preferably room temperature, for from 6 to 24 hours. For the preparation of the aglycone, 1% acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acids listed above are appropriate for this process, and again sulfuric acid is the preferred acid.

It has also been observed that the monosaccharide is prepared during the course of the reaction used to remove the trialkylsilyl protecting group. Since acid catalysis is used to remove the protecting group, this is expected. However, in such cases, both the desired product and the monosaccharide are prepared and they can be readily separated using the above-described techniques. In the preparation of the 4' or 4" keto or amino substituted compounds, the avermectin starting materials or the 8,9-cyclopropyl derivatives are oxidized at the 4"-position to the corresponding keto compound. During the procedure the presence of any hydroxy groups at the 5 and 23-position will require that such hydroxy groups be protected in order that they too are not oxidized. The 7-hydroxy group is very unreactive and need not be protected. The procedure used to prepare the protected intermediates are described above. The oxidation reaction is carried out in an inert solvent such as methylene chloride using oxalyl chloride or trifluoroacetic anhydride in dimethylsulfoxide as the oxidizing agent. Additionally N-chlorosuccinimide in dimethylsulfide may be employed. The reaction proceeds by dissolving the oxalyl chloride or trifluoroacetic anhydride and dimethylsulfoxide (or other oxidizing reagents) in methylene chloride and cooling to from −50° to −80° C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is ten allowed to warm to room temperature over a period of from ½ to 1 hour. The 4' or 4"-keto compound is isolated using techniques known to those skilled in the art.

In the next step, the 4' or 4''-keto compound is aminated to prepare the unsubstituted amino compound ($R_6$=$R_7$=hydrogen). The reaction is carried out in an inert solvent such as methanol at from $-10°$ to $+25°$ C. using ammonium salts and sodium cyanoborohydride as the aminating and reducing reagents, respectively. The reaction is complete in from 15 minutes to 24 hours and the product 4''-deoxy-4''-amino compound is isolated using techniques known to those skilled in the art. Suitable ammonium salts are the acetate, propionate, benzoate and the like. The acetate is preferred.

As a variation to the foregoing animation reaction, methyl ammonium salts could be used in place of the ammonium salts to prepare the monomethyl substituted compound directly. The same reagents, salts and reaction conditions as described above can be used for such a reaction.

The substitution reaction wherein the substituent is an acyl function is carried out using an acylating reagent in the presence of a base in an inert solvent. The preferred acylating reagents are loweralkanoyl anhydrides, loweralkanoyl halides, substituted benzene sulfonyl chlorides, lower alkyl sulfonyl chlorides, and the like. The reaction is carried out in an inert solvent such as methylene chloride in the presence of a non-reactive base such as pyridine or triethylamine in order to neutralize the acid produced during the course of the reaction. The reaction temperature is from $-10°$ to $25°$ C. and the reaction is complete in from 5 minutes to 1 hour. The product is isolated using known techniques.

The reaction for the preparation of the 4'-or 4''-deoxy-4'- or 4''-dialkylamino compounds is carried out using the alkylating reaction conditions of an excess of a carbonyl compound, preferably formaldehyde and a reducing agent such as sodium cyano borohydride, in methanol. The reaction is carried out in a solvent suitable to dissolve the organic starting material using excess aqueous formaldehyde along with the presence of a small amount of acid such as acetic acid to facilitate the reaction. The reaction is carried out at from $-10°$ to $+25°$ C. with the solution of the avermectin compound in methanol added dropwise over a period of from 30 to 60 minutes to the alkylating reagent mixture and the product is isolated using known techniques.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesphagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as two-spotted spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

In the isolation of the avermectin compounds, which serve as starting materials for the instant processes, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a small percent by weight, and the structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like.

Being amorphous, the compounds are not characterized by sharp melting points, however, the chromatographic and analytical methods employed indicate that the compounds are pure.

In the following examples, the various starting materials therefor are avermectin compounds or derivatives of avermectin compounds. The avermectin compounds and the preparation and isolation thereof from fermentation broths are described in U.S. Pat. No. 4,310,519 issued Jan. 12, 1982. The selective 22,23-dihydro derivatives of avermectin compounds are described in U.S. Pat. No. 4,199,569 issued Apr. 22, 1980. The aglycone and monosaccharide derivatives of avermectin compounds are described in U.S. Pat. No. 4,206,205 issued Jan. 3, 1980. The 13-deoxy compounds are described in U.S. Pat. Nos. 4,171,314 and 4,175,571. The milbemycin compounds are described in U.S. Pat. No. 3,950,360.

EXAMPLE 1

5-O-(tert-Butyldimethylsilyl)-8,9-dihydro-8,9-methanoavermectin B1a

To a hot (100° C.) solution of $Cu(OAc)_2.H_2O$ (9.4 mg) in 1 ml of glacial acetic acid was added 163 mg of powdered zinc metal. The mixture was vigorously stirred for a few minutes and then permitted to cool. The solvent was carefully removed with a pipette and the couple rinsed with glacial acetic acid (2×1 ml) and then with anhydrous ether (4×2 ml). The couple was suspended in 3 ml of dry ether to which was added 197 mg of 5-O-(tert-butyldimethylsilyl)avermectin B1a and 120 μl of diiodomethane. The reaction mixture was heated at reflux under nitrogen for 6 hours. After 4 hours an additional 40 μl of diiodomethane was added. The reaction mixture was diluted with 60 ml of ether and 40 ml of saturated aqueous ammonium chloride. The mixture was stirred and then filtered through diatomaceous earth. The layers were separated and the etheral layer washed with sodium bicarbonate solution, water, and brine. The solution was dried with sodium sulfate, concentrated, and then chromatographed on silica gel (3:1 hexanes:ethyl acetate) to give two monocyclopropyl adducts and a bicyclopropy adduct; 5-O-(tert-butyldimethylsilyl)-8,9-dihydro-8,9-methanoavermectin B1a, 21.3 mg; 5-O-(tert-butyldimethylsilyl) 3,4-dihydro-3,4-methanoavermectin B1a, 98.1 mg; 5-O-(tert-butyldimethylsilyl)-3,4,8,9-tetrahydro-3,4-methano-8,9-methanoavermectin B1a, 35.8 mg. The products were identified by high field proton and $^{13}C$ NMR studies in conjunction with mass spectroscopy results.

EXAMPLE 2

5-O-(tert-Butyldimethylsilyl)-8,9-dihydro-8,9-methanoavermectin B1b

The zinc-copper couple, prepared as in Example 1, is suspended in 3 ml of dry ether to which 5-O-(tert-butyldimethylsilyl)avermectin B1b (197 mg) is added. Diiodomethane (160 μl) is added in two portions and the reaction mixture is heated at reflux until the reaction is completed as determined by HPLC (reverse phase column). The reaction is then diluted with ether (60 ml) and saturated aqueous ammonium chloride (40 ml). The zinc precipitate is collected by filtration and the resulting two-phase filtrate is separated. The ethereal layer is further washed with $NaHCO_3$ solution, water, and brine. The solution is dried with sodium sulfate, concentrated and chromatographed on silica gel to give the desired product, 5-O-(tert-butyldimethylsilyl)-8,9-dihydro8,9-methanoavermectin B1b.

EXAMPLE 3

8,9-Dihydro-8,9-methanoavermectin B1a and 8,9-dihydro8,9-methanoavermectin B1a monosaccharide A solution of 5-O-(tert-butyldimethylsilyl)8,9-dihydro-8,9-methanoavermectin B1a (20 mg) from Example 1 in 2 ml of methanol containing 0.5% (w/w) of p-toluenesulfonic acid hydrate was stirred for 55 minutes at room temperature. The reaction mixture was then diluted with 40 ml of $CH_2Cl_2$ and extracted with 5% aqueous sodium bicarbonate solution (2×15 ml) and water (1×15 ml). The organic solution was dried with sodium sulfate, concentrated and chromatographed on a 500 μ silica gel TLC plate with ethyl acetate:hexanes (1:1) as eluant. Two products were isolated and characterized (NMR, mass spec): 8,9-dihydro-8,9-methanoavermectin B1a, $R_f=.20$, 8.3 mg; and 8,9-dihydro-8,9-methanoavermectin B1a monosaccharide, $R_f=.28$, 5.5 mg.

EXAMPLE 4

8,9-Dihydro-8,9-methanoavermectin B1a

A stock solution (1 ml) of HF.pyridine in tetrahydrofuran (2 ml of commercial (Aldrich Chemical Co.) (HF).pyridine diluted with 14 ml of tetrahydro-furan and 4 ml of pyridine) was added to 21 mg of 5-O-(tert-butyldimethylsilyl)-8,9-dihydro-8,9-methanoavermectin B1a (Example 1) in a polypropylene vial with rubber septum. The mixture is stirred overnight under nitrogen. The reaction mixture is added to an ice-cooled aqueous solution of sodium bicarbonate (200 ml) and extracted with ethyl acetate (3×20 ml). The organic layers are then combined and washed with 0.5N hydrochloric acid (20 ml), water (20 ml), saturated sodium bicarbonate solution (20 ml), and finally brine (20 ml). The solution is dried with sodium sulfate, concentrated, and chromatographed on a 1000 micron silica gel TLC plate (1:1 hexane:ethylacetate) to give 13 mg of the desired product, 8,9-dihydro-8,9-methanoavermectin B1a.

EXAMPLE 5

8,9-Dihydro-8,9-methanoavermectin B1b and 8,9-dihydro-8,9-methanoavermectin B1b monosaccharide A solution of 5-O-(tert-butyldimethylsilyl)8,9-dihydro-8,9-methanoavermectin B1b (100 mg) from Example 2 in 1 ml of methanol containing 0.5% (w/w) of p-toluenesulfonic acid monohydrate is stirred at room temperature until TLC indicates reaction is completed. The reaction mixture is diluted with methylene chloride (20 ml) and extracted with 5% aqueous sodium bicarbonate (2×15 ml) and water (1×15 ml). The organic layers are dried with sodium sulfate, concentrated, and chromatographed on silica gel to give two major products: 8,9-dihydro-8,9-methanoavermectin B1b and 8,9-dihydro-8,9-methanoavermectin B1b monosaccharide.

EXAMPLE 6

5-O-(tert-Butyldimethylsilyl)-8,9,22,23-tetrahydro-8,9-methanoavermectin B1a/B1b The zinc-copper couple was prepared as in Example 1 and suspended in 3 ml of anhydrous diethyl ether. To this mixture was added 198 mg of 5-O-(tertbutyldimethylsilyl)-22,23-dihydroavermectin B1a/B1b followed by diiodomethane (90 μl). The reaction mixture was heated at reflux under nitrogen. After 4 hours, an additional 40 μl of diiodomethane was added. The reaction mixture was heated at reflux a total of 9 hours and then permitted to stir overnight at room temperature. Ther reaction mixture was diluted with 60 ml of ether and 30 ml of saturated ammonium chloride solution. The mixture was stirred and then filtered through diatomaceous earth. The layers were separated and the organic layer washed with 5% sodium bicarbonate solution, water, and then brine. The solution was dried with sodium sulfate, concentrated and chromatographed on a silica gel column (MPLC) with 3:1 hexanes:ethyl acetate to give: 5-O-(tert-butyldimethylsilyl)-8,9,22,23-tetrahydro-8,9-methanoavermectin B1a/B1b, 18.4 mg; 5-O-(tert-butyldimethylsilyl)-3,4,8,9,22,23-hexahydro-3,4-methano-8,9-methanoavermectin B1a/B1b, 54.6 mg; 5-O-((tert-butyldimethyl-silyl)-3,4,22,23-tetrahydro-3,4-methanoavermectin B1a/B1b, 57.2 mg. The adducts were characterized by $^1$H NMR and mass spectroscopy data.

EXAMPLE 7

8,9,22,23-Tetrahydro-8,9-methanoavermectin B1a/B1b and 8,9,22,23-tetrahydro-8,9-methanoavermectin B1a/B1b monosaccharide A solution of 5-O-(tert-butyldimethylsilyl)-8,9,22,23-tetrahydro-8,9-methanoavermectin B1a/B1b (15 mg) (Example 6) in 1.5 ml of methanol containing 0.5% (w/w) of p-toluenesulfonic acid monohydrate was stirred for 1 hour at room temperature. The reaction mixture was diluted with 30 ml of dichloromethane and extracted with aqueous 5% sodium bicarbonate solution (2×15 ml), water (1×15 ml), and then dried with sodium sulfate. The organic layer was concentrated and then chromatographed on a silica gel TLC plate (500 μ) [1:1 ethyl acetate:hexanes]. Two products were isolated and characterized by NMR and mass spectroscopy as 8,9,22,23-tetrahydro-8,9-methanoavermectin B1a/B1b, $R_f$=0.24, 4.6 mg; 8,9,22,23-tetrahydro-8,9-methanoavermectin B1a/B1b monosaccharide, $R_f$=0.33, 3.7 mg.

EXAMPLE 8

8,9-Dihydro-8,9-methanoavermectin A1a/A1b

The zinc-copper couple, prepared as in Example 1, is suspended in 3 ml of anhydrous ether. To this mixture, avermectin A1a/A1b (180 mg) is added along with diiodomethane (160 μl in two portions over 4 hours). The reaction mixture is heated at reflux until the reaction is completed (HPLC). The reaction mixture is diluted with ether (60 ml) and saturated aqueous ammonium chloride (40 ml). The mixture is filtered through diatomaceous earth and the layers separated. The organic layer is washed with aqueous sodium bicarbonate solution, water, and brine. The solution is dried with sodium sulfate, concentrated, and chromatographed on silica gel to give the desired product, 8,9-dihydro-8,9-methanoavermectin A1a/A1b.

EXAMPLE 9

4″,5-di-O-(tert-Butyldimethylsilyl)-8,9-dihydro-8,9-methanoavermectin B2a/B2b To a suspension of the zinc-copper couple, as prepared in Example 1, in 3 ml of dry ether, 4″,5-di-O-(tert-butyldimethylsilyl)avermectin B2a/B2b (prepared by reacting avermectin B2a/B2b with an excess of tert-butyldimethylsilyl chloride and imidazole in dimethylformamide), 200 mg, is added followed by diiodomethane (160 μl added in increments over 4 hours). The mixture is heated at reflux until HPLC indicates the reaction is done. Work-up is similar to that described in Example 1. Chromatography affords the desired product, 4″,5-di-O-(tert-butyldimethylsilyl)-8,9-dihydro-8,9-methanoavermectin B2a/B2b.

EXAMPLE 10

8,9-Dihydro-8,9-methanoavermectin B2a/B1b

A stock solution (1 ml) of HF.pyridine in tetrahydrofuran (see Example 4) is added to 4″,5-di-O-(tert-butyldimethylsilyl)-8,9-dihydro-8,9-methanoavermectin B2a/B2b from Example 9, in a polypropylene vial with rubber septum. The reaction mixture is stirred for 48 hours and added to an ice-cooled aqueous solution of sodium bicarbonate (20 ml). The mixture is extracted with ethyl acetate (3×20 ml), the organic layers backwashed with 0.5N hydrochloric acid, water, and 5% sodium bicarbonate solution. The solution is dried with sodium sulfate, concentrated, and chromatographed on a silica gel TLC plate to give 8,9-dihydro-8,9-methanoavermectin B2a/B2b.

EXAMPLE 11

5-O-(tert-Butyldimethylsilyl)-8,9-dihydro-8,9-methanoavermectin B1a/B1b aglycone The zinc-copper couple, prepared as in Example 1, is suspended in 3 ml of anhydrous diethyl ether. To this suspension, 5-O-(tert-butyldimethylsilyl)avermectin B1a/B1b aglycone, 150 mg (prepared by reacting avermectin B1a/B1b aglycone with 3 equivalents of tert-butyldimethylsilyl chloride and 6 equivalents of imidazole in dimethylformamide), is added followed by diiodomethane (160 μl added in increments over 4 hours). The reaction mixture is heated at reflux under nitrogen until HPLC indicates consumption of starting material. The reaction mixture is diluted with ether (60 ml) and saturated ammonium chloride solution (40 ml). The mixture is filtered and the layers separated. The ether layer is washed with 5% sodium bicarbonate solution, water, and brine. The solution is dried with sodium sulfate, concentrated, and chromatographed on silica gel (MPLC) to give the desired product, 5-O-(tert-butyldimethylsilyl)-8,9-dihydro-8,9-methanoavermectin B1a/b aglycone.

EXAMPLE 12

8,9-Dihydro-8,9-methanoavermectin B1a/B1b aglycone

A methanolic solution (4 ml) of 5-O-(tert-butyldimethylsilyl)-8,9-dihydro-8,9-methanoavermectin B1a/B1b aglycone (4 mg) from Example 11, containing 0.5% (w/w) p-toluene sulfonic acid monohydrate is stirred at room temperature for 1 hour. The reaction mixture is diluted with methylene chloride (80 ml) and extracted with 5% sodium bicarbonate solution (2x30 ml) and water (1x30 ml). The organic layer is dried with sodium sulfate, concentrated and chromatographed on silica gel to give 8,9-dihydro-8,9-methanoavermectin B1a/B1b aglycone.

EXAMPLE 13

5-O-(tert-Butyldimethylsilyl)-13-deoxy-8,9,22,23-tetrahydro-8,9-methanoavermectin B1a/B1b aglycone The zinc-copper couple, as prepared in Example 1, is suspended in 3 ml of dry ether. 5-O-(tert-Butyldimethylsilyl)-13-deoxy-22,23-dihydro-avermectin B1a/B1b aglycone [H. Mrozik et al., Tetrahedron Lett., 24, 533 (1983)], 150 mg, is added to the suspension along with diiodomethane (160 μl added in large portions over 4 hours). The reaction mixture is then heated at reflux under nitrogen until all starting material has been consumed as indicated by HPLC. The reaction mixture is diluted with ether (80 ml) and saturated aqueous ammonium chloride (50 ml). The two phase solution is filtered through diatomaceous earth and then separated. The organic layer is washed with 5% sodium bicarbonate solution, water, and brine. The solution is dried with sodium sulfate, concentrated, and chromatographed on silica gel to give 5-O-(tert-butyldimethylsilyl)-13-deoxy-8,9,22,23-tetrahydro-8,9-methanoavermectin B1a/B1b aglycone.

EXAMPLE 14

13-Deoxy-8,9,22,23-tetrahydro-8,9-methanoavermectin B1a/B1b aglycone

A solution of 5-O-(tert-butyldimethylsilyl)-13-deoxy-8,9,22,23-tetrahydro-8,9-methanoavermectin B1a/B1b aglycone, 20 mg from Example 13, in 2 ml of methanol containing 0.5% (w/w) of p-toluenesulfonic acid monohydrate is stirred at room temperature for approximately 1 hour. The reaction mixture is diluted with methylene chloride (50 ml) and extracted with 5% sodium bicarbonate solution (2×15 ml) and water (1×25 ml). The organic layer is dried with sodium sulfate, concentrated, and chromatographed on silica gel to give 13-deoxy-8,9,22,23-tetrahydro-8,9-methanoavermectin B1a/B1b aglycone.

EXAMPLE 15

4″-Keto-5-O-(tert-Butyldimethylsilyl)-8,9-dihydro-8,9-methanoavermectin B1a/B1b To a solution of oxalyl chloride (57 ml) in 1.5 ml of dry methylene chloride at −60° under nitrogen, a solution of dimethylsulfoxide (DMSO) in 0.8 ml of methylene chloride is added. The reaction mixture is stirred for a few minutes at −60° C. and a solution of 5-O-(tert-butyldimethylsilyl)-8,9-dihydro-8,9-methanoavermectin B1a/B1b from Examples 1 and 2, (296 mg) in 1.5 ml of methylene chloride is added over 5 minutes. The reaction mixture is stirred for 30 minutes at −60° C. after which 0.41 ml of triethylamine is added and the mixture permitted to warm to room temperature. The reaction mixture is transferred to a separatory funnel, diluted with water (30 ml) and the layers separated. The aqueous layer is further extracted with methylene chloride (3×20 ml) and the combined organic layers are back-washed with 0.5 N hydrochloric acid, 5% aqueous sodium bicarbonate solution, water, and brine. The organic portion is dried with magnesium sulfate, concentrated, and chromatographed on silica gel to give 4″-keto-5-O-(tert-butyldimethylsilyl)-8,9-dihydro-8,9-methanoavermectin B1a/B1b.

EXAMPLE 16

4″-Amino-4″-deoxy-5-O-(tert-butyldimethylsilyl)-8,9-dihydro-8,9-methanoavermectin B1a/B1b To a solution of 4″-keto-5-O-(tert-butyldimethylsilyl)-8,9-dihydro-8,9-methanoavermectin B1a/B1b (178 mg) from Example 15 and ammonium acetate (0.137 g) in 3 ml of absolute methanol, sodium cyanoborohydride (30 mg) can be added. The reaction mixture is then stirred overnight under nitrogen. The reaction is terminated by adding the mixture to 20 ml of 20% aqueous sodium carbonate. The mixture is then extracted with ethyl acetate (4×25 ml). The combined organic layers are back-washed with water and brine. The organic fraction is dried with magnesium sulfate, concentrated, and chromatographed on silica gel to give an epimeric mixture of 4″-amino-4″-deoxy-5-O-(tert-butyldimethylsilyl)-8,9-dihydro-8,9-methanoavermectin B1a/B1b.

EXAMPLE 17

4″-Amino-4″-deoxy-8,9-dihydro-8,9-methanoavermectin B1a/b

A stock solution (1 ml) of HF.pyridine in tetrahydrofuran (see Example 4) can be added to 10 mg of 4″-amino-4″-deoxy-5-O-(tert-butyldimethylsilyl)-8,9-dihydro-8,9-methanoavermectin B1a/B1b (Example 16) in a polypropylene vial fitted with a rubber septum. The mixture is stirred overnight under nitrogen. The reaction mixture can then be added to an ice-cooled, saturated aqueous solution of sodium bicarbonate (20 ml) and the resulting solution extracted with ethyl acetate (3×20 ml). The combined ethyl acetate layers are washed with 0.5N hydrochloric acid (20 ml), water (20 ml), saturated sodium bicarbonate solution (20 ml), and finally brine (20 ml). The solution is dried with sodium sulfate, concentrated, and chromatographed on a preparative silica gel TLC plate to give 4″-amino-4″-deoxy-8,9-dihydro-8,9-methanoavermectin B1a/B1b.

EXAMPLE 18

4″-Acetylamino-4″-deoxy-5-O-(tert-butyldimethylsilyl)-8,9-dihydro-8,9-methanoavermectin B1a/B1b To a cold (ice) solution of 4 ″-amino-4″-deoxy-5-O-(tert-butyldimethylsilyl)-8,9-dihydro-8,9-methanoavermectin B1a/B1b (59 mg from Example 16) in 2.5 ml of dry methylene chloride, a solution of 11 μl of acetic anhydride and 30 μl of pyridine in 1 ml of methylene chloride is added. The reaction mixture is stirred for 30 minutes and added to 3 ml of 0.25% hydrochloric acid. The organic layer is further washed with water (3 ml), 5% sodium bicarbonate solution (3 ml), and brine (3 ml). The organic solution is dried with magnesium sulfate, concentrated, and purified on a preparative TLC plate (silica gel) to give 4″-acetylamino-4″-deoxy-5-O-(tert-butyldimethylsilyl)-8,9-dihydro-8,9-methanoavermectin B1a/B1b.

EXAMPLE 19

4″-Acetylamino-4″-deoxy-8,9-dihydro-8,9-methanoavermectin B1a/B1b

A solution of 4″-acetylamino-4″-deoxy-5-O-(tert-butyldimethylsilyl)-8,9-dihydro-8,9-methanoavermectin B1a/B1b (20 mg from Example 18) in 2 ml of methanol containing 0.5% (w/w) of p-toluenesulfonic acid hydrate is stirred for 1 hour at room temperature. The reaction mixture is diluted with 40 ml of methylene chloride and extracted with 5% aqueous sodium bicarbonate solution (2×15 ml) and water (1×15 ml). The organic solution is dried with magnesium sulfate, concentrated, and chromatographed on a preparative TLC plate to give the desired product, 4''-acetylamino-4''-deoxy-8,9-dihydro-8,9-methanoavermectin B1a/B1b.

What is claimed is:

1. A compound having the formula:

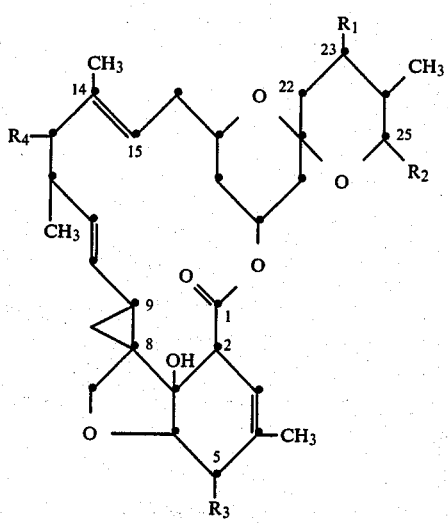

wherein the broken line at the 22,23-position indicates a single or a double bond;

$R_1$ is hydrogen or hydroxy provided that $R_1$ is present only when the broken line at the 22,23-position indicates a single bond;

$R_2$ is methyl, ethyl, iso-propyl or sec-butyl;

$R_3$ is hydroxy or methoxy;

$R_4$ is hydrogen, hydroxy

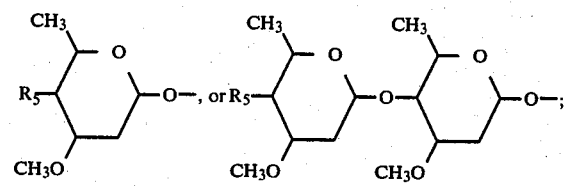

$R_5$ is hydroxy, keto or $-NR_6R_7$ $R_6$ and $R_7$ are independently hydrogen, lower alkyl, loweralkanoyl, loweralkyl sulfonyl, or substituted benzenesulfonyl wherein the substituent is halogen; and the trisubstituted silyl protected hydroxy derivatives thereof.

2. The compound of claim 1 which is 8,9-dihydro-8,9-methanoavermectin B1a and B1b.

3. The compound of claim 1 which is 8,9-dihydro-8,9-methanoavermectin B1a and B1b monosaccharide.

4. The compound of claim 1 which is 8, 9, 22, 23-tetrahydro-8,9-methanoavermectin B1a and B1b.

5. The compound of claim 1 which is 8, 9, 22, 23-tetrahydro-8,9-methanoavermectin B1a and B1b monosaccharide.

6. The compound of claim 1 which is 13-deoxy-8,9,22,23-tetrahydro-8,9-methanoavermectin B1a/B1b aglycone.

7. A process for the preparation of the compounds of claim 1 which comprises treating the compound with an 8, 9 double bond in an organic solvent with an iodohalomethane and an activated form of zinc and heating at from room temperature to the reflux temperature of the reaction mixture.

8. A method for the treatment of helmintic ectoparasitic, insect and acarid parasitic infections which comprises orally or parenterally administering to an animal infected with such parasites an effective amount of a compound of claim 1.

9. A composition useful for treating animals infected with helmintic, ectoparasitic, insect and acarid parasites which comprises an inert carrier and an effective amount of a compound of claim 1.

10. A method for the treatment of household and agricultural insect pests which comprises applying to an area infested with such insect pests, an effective amount of a compund of claim 1.

11. A composition useful for treating areas infected with household or agricultural insect pests which comprises an inert carrier and an effective amount of a compound of claim 1.

* * * * *